United States Patent

Plant Pat. 3,804
Patented Nov. 11, 1975

3,804

ROSE PLANT—MEIRINGA VARIETY

Marie-Louise Meilland and Alain A. Meilland, Antibes, and Michele Meilland Richardier, Tassin-la-Demi-Lune, France, assignors to The Conard-Pyle Company, West Grove, Pa.

Filed Oct. 24, 1974, Ser. No. 517,820
Claims priority, application Morocco, Dec. 7, 1973, 16,626
Int. Cl. A01h 5/00
U.S. Cl. Plt.—14 1 Claim

ABSTRACT OF THE DISCLOSURE

A new and distinct variety of rose plant of the hybrid tea class, originated by crossing an unnamed and unpatented seedling with the rose variety Jack Frost, and obtaining an extreme purity of white color of its blooms, with firm and resistance texture of its petals, capable of forcing, with great yield capacity of flowers of quality.

SUMMARY OF THE INVENTION

The object of the present invention is a variety of rose plant, of the hybrid tea class, with white, double flowers, which is distinguishable from varieties already known in that class and of that color, on account of the following characteristics:

extreme purity of the white color of its blooms;
firm and resistance texture of the petals;
particular aptitude of the plant to forcing; and
great yield capacity of flowers of quality.

Because of the characteristics mentioned above, the present invention answers the needs of the horticultural industry for all uses, and more especially for the production of cut flowers.

The aim that the applicants had in view was to create a variety which would derive the aforementioned advantages from the genetic combination of two genitors whose previous and respective study would allow them to expect, in their common descent, the appearance of the characters sought.

The rose chosen as female genitor was an unknown and unpatented seedling, the product of the pollination of the variety MEIchim–257F, more generally known in the trade under the name of Carina, by the variety MEban–551, more generally known in the trade under the name Message; the rose chosen as male genitor was the variety known in the trade by the name of Jack Frost.

The operation of artificial pollination performed by the applicants can therefore be expressed by the following schematic formula:

(MEIchim–257F "Carina" × Meban–551 "Message") × Jack Frost

From the fruits thus formed by this controlled pollination, seeds were extracted whose cells were the result of the combination of factors which existed in the cells of the genitors and by virtue of which these genitors had been precisely chosen.

After having sown these seeds, the applicants obtained 380 small plants, physically and biologically distinct from one another.

After having eliminated all of the plants which were deficient or abnormal, or whose characters were too remote from the ones they were seeking, the applicants proceeded with the grafting of the remaining plants, in order to carry on their work exclusively on rose-plants which were, in every respect, in conformity with those produced and commercialized by professional nurserymen.

From then on, they undertook the selective study of the plants thus formed; during which study they were led to eliminate systematically all the rose plants which had been grafted, with the exception of one only, which was the closest to the desired goal.

This variety had flowers of a very pure white; their petals were remarkably firm and resistant; this variety asserted itself particularly suited to forcing.

Technical tests (grafting inside or outside, with dormant eye buds, started eye buds, in heated glass houses, in cold glass houses, on various understocks) were then made in order to ascertain the behavior of the variety just created.

The results were conclusive and underlined the importance of creating this variety with a view to its industrial exploitation, for all uses, especially for the production of cut flowers.

The characters and properties of this new variety, obtained as indicated above, are strictly transmissible by agamic means, also called "asexual means," i.e. by any means of vegetative propagation, and in particular by grafting an "eye" which will be called in the trade by the name of eye of Meiringa 0854F, and which will be found on industrial plants as well as on cut stems delivered subsequently by the trade. Thus will be obtained once again the rose variety which is the object of the invention, and whose botanical and descriptive characteristics, noted on plants under glass, are given below.

BRIEF DESCRIPTION OF DRAWINGS

The accompanying drawings show as nearly true as it is reasonably possible to make the same in a color illustration of this character, typical specimens of the flowers and foliage, illustrating in FIG. 1, a specimen of a young shoot.

DETAILED DESCRIPTION OF DISCLOSURE

Figures 1, 2, 3, 4, 5, 6, 7, 8, 9, 10, 11, 12, 13:
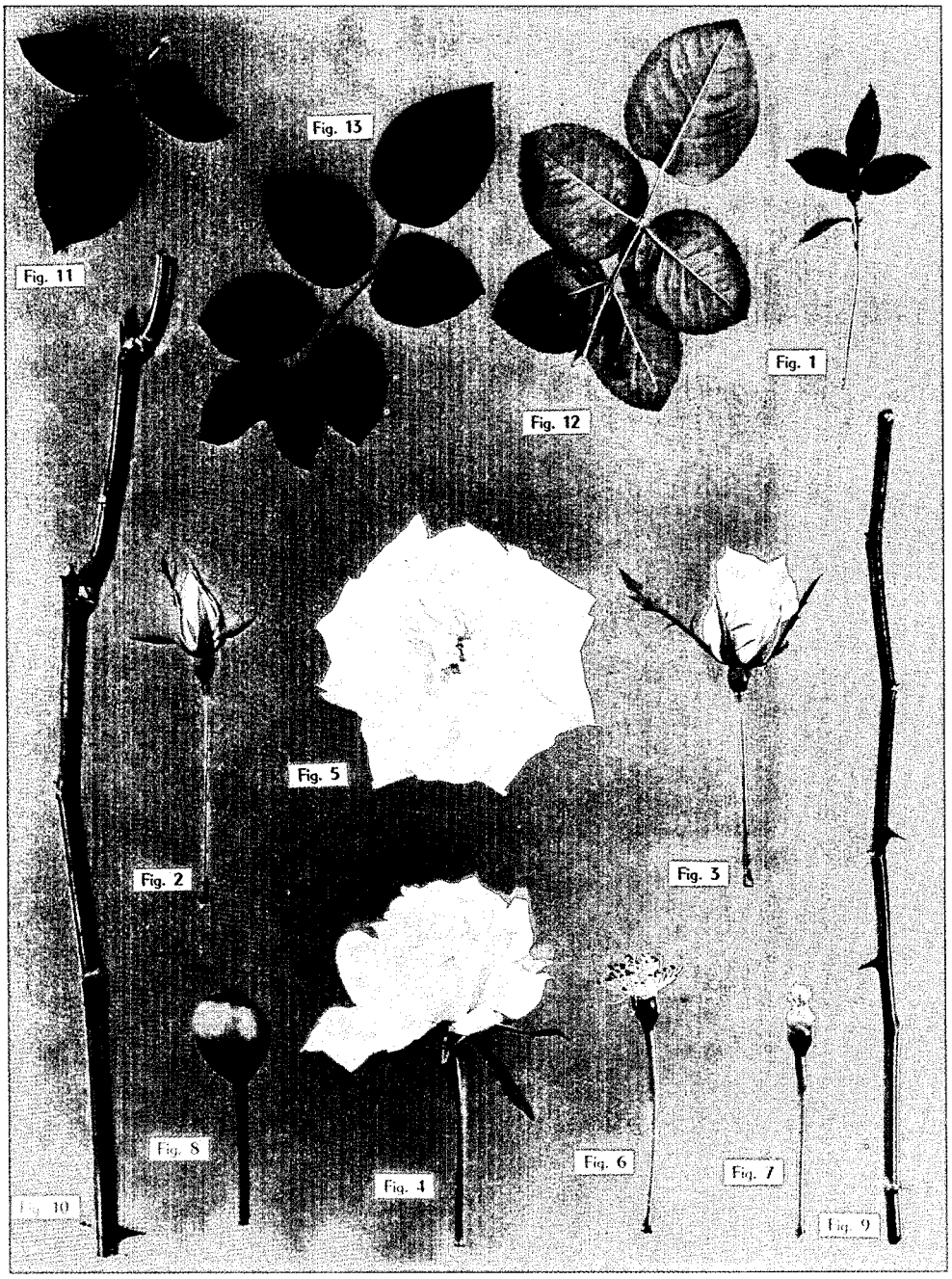
FIG. 2, a specimen of a bud when sepals start to open.
FIG. 3, a specimen of bud when petals start to open.
FIG. 4, a specimen of a flower in the course of opening.
FIG. 5, a specimen of an open flower, flat view, upper surface.
FIG. 6, a specimen of a receptacle showing the disposition of the stamens.
FIG. 7, a specimen of a receptacle showing the disposition of the pistils.
FIG. 8, a specimen of a mature fruit.
FIG. 9, a portion of a flowering stem.
FIG. 10, a portion of a main branch.
FIG. 11, a specimen of leaf with three folioles, upper surface.
FIG. 12, a specimen of leaf with five folioles, under surface.
FIG. 13, a specimen of leaf with seven folioles, upper surface.

The chart used for the identification of the colors is that of the Royal Horticultural Society (R.H.S. Color Chart). The terminology preceding the numbered references, proper to this chart, has been added to designate, in common terms, the corresponding colors.

Class: Hybrid tea.
Plant:
*Development.*—On the basis of the cutting back of the plants to Om. 85 (about) the length of the flowering stems can be said to be between 50 and 70 centimeters.
*Habit.*—Straight.
Branches:
*Color.*—Young stems: Light green 146/A (yellow green group). Mature wood: Light green 146/B more or less intense and veined with 146/A.
*Prickles.*—Shape: Upper edge: straight, tapered. Lower edge: Straight to slightly concave. Base: Elliptical, narrow. Size: Rather small but elongated. Quantity: Small. Color: On young stems: some rare prickles are greenish at their base, then straw color (common terms). On mature wood: Havana (more or less dark) (common term).

Leaves:

*Stipules.*—Adnate, pectinate, fairly wide and linear.

*Petiole.*—Obverse: the edges of the rib are medium green and slightly glandular. Reverse: light green, with a few small greenish-white prickles, more generally straight than curved.

It forms, with the stem, an angle between 45 and 90°.

*Folioles.*—Number: 3–5–7.

Shape: (1st pair, starting from the top, of a leaf placed at the average ⅓ of a flower-bearing branch). Base. Rounded, asymmetrical. Top: Wide, symmetrical. Shape, as a whole: Elliptical. Teeth: Single and fine. Texture: Leathery, the latent veins are very prominent on the reverse. General effect: Fairly ample foliage, moderately dense, more dull than shiny. Color: Young foliage: Upper surface: Medium green 137/B (green group). Undersurface: Light green 191/B (greyed-green group). Adult foliage: Upper surface: Medium green 137/B (green group). Undersurface: Light green 191/B (greyed-green group).

It is to be noted that at the outset of the growth, as also during the course of vegetation, the foliage of the young shoots is light green encircled with reddish brown.

Inflorescence:

*Number of flowers.*—One flower per stem.

*Peduncle.*—Straight, good stiffness, slightly glandular, light green. Length: From 5 to 7 cms.

*Sepals.*—Downy, greenish white inside, light green and smooth outside, the edges generally show a few appendages, the tip is quite tapered.

*Bud.*—Shape: pointed, tapered. Length: 32 millimeters outside of the calyx, when the first petal opens. Size: Medium. Color: When opening: Obverse: White 157/B (green-white group). Reverse: White 155/B (white group) shaded with light green 145/B (yellow-green group) at the base and on about half of the median nerve starting at base.

Flower: Form: First of all a little cylindrical, with opened out edges and a hollow center, then open, with center more loosened, protruding petals, conspicuous stamens, final form as a somewhat flattened out cup.

Double flower:

*Diameter.*—10 cms.

*Color.*—When opening: Inside: White 155/D (white group), slightly tinted, in depth, with a yellowish color, 10/D (yellow group). Outside: White 155/D (white group) very slightly greenish close to the sepals. During the course of opening: Inside: White 155/D (white group.) outside: White 155/D (white group).

*When fully open.*—Inside: White 155D (white group) Outside: White 155/D (white group).

*Fragrance.*—Without.

*Lasting quality when cut.*—Long.

*Corolla.*—Petals: Texture: Very firm; the unguis is yellowish, narrow, more noticeable on the inside than on the outside. Shape: The petals on the exterior periphery are rounded with lateral edge slightly reflexed and pointed tip; those in the interior have a wedge-shaped base, and a tip which is a little wrinkled and wavy, Number: 35 to 40. They drop off cleanly. Stamens: Number: 90 on an average. Anthers: Normal, yellow. Filaments: Yellowish. Pistils: Number: 80 on an average. Stigmas: Pinkish white, quite distinctly over the orifice of the receptacle and on the same level as that of the anthers. Styles: Free, rather strangled and twisted when coming out of the receptacle, yellowish then gradually becoming reddish. Receptacle: Light green, lengthwise it is narrow and in the shape of a pitcher; when matured, the fruit is pear-shaped, and orange 30/D, more or less shaded with 30/C (orange-red group).

Development:

*Vegetation.*—Vigorous.

*Flowering.*—Practically continuous.

*Resistance to diseases.*—Good resistance.

We claim:

1. A new and distinct variety of rose plant of the hybrid tea class, substantially as illustrated and described, distinguished as to novelty, from the physical point of view, the plant, with light green mature wood, is erect, the flower is double, white, the petals are very firm and have a yellowish unguis whose color is more noticeable inside than outside; from the biological point of view, this rose plant grows vigorously, has a particular aptitude for forcing, its flowers last a long time when cut, and the petals drop off cleanly.

No references cited.

ROBERT E. BAGWILL, Primary Examiner